United States Patent [19]

Wilson et al.

[11] 4,188,535

[45] Feb. 12, 1980

[54] METHOD AND APPARATUS FOR MONITORING DENSITY FLUCTUATIONS IN MATERIAL FLOWING SPIRALLY WITHIN A HYDROCYCLONE

[76] Inventors: Peter C. Wilson; Robert P. Hughart, both of 2045 W. 9th Ave., Denver, Colo. 80204

[21] Appl. No.: 848,024

[22] Filed: Nov. 3, 1977

[51] Int. Cl.² .......................................... G01N 23/00
[52] U.S. Cl. .................................... 250/359; 250/356
[58] Field of Search ........... 250/304, 308, 356, 358 R, 250/359, 360, 432 R, 434, 435; 209/211; 210/512 M

[56] References Cited

U.S. PATENT DOCUMENTS

| 3,912,579 | 10/1975 | Braun | 209/211 |
| 4,010,369 | 3/1977 | Daellenbach et al. | 250/356 |
| 4,044,259 | 8/1977 | Wyton et al. | 250/360 |

Primary Examiner—Davis L. Willis
Attorney, Agent, or Firm—Burton & Dorr

[57] ABSTRACT

A method and apparatus for monitoring density fluctuations in a spiralling flow within a hydrocyclone. The invention involves the use of a nuclear density gauge which directs a beam of radiation asymmetrically across the hydrocyclone away from the centrally located air column. This air column within the hydrocyclone is created by the spiralling or cyclonic action of the flow and exists when the hydrocyclone is in operation. In a preferred embodiment, the flow is particulate solids in a carrier liquid such as water which has a substantially constant specific gravity so that the fluctuations in the intensity of the radiation received at the detector are inversely proportional to the amount of particulate solids in the flow. In one embodiment, the radiation is directed along a path substantially perpendicular to the axis of symmetry of the hydrocyclone and in another embodiment, the radiation is directed along a path at an inclined angle to the axis. Unlike past arrangements in which the nuclear density gauge is used only as an on-off type switch or warning device reacting to the absence or presence of the air column at a particular location within the hydrocyclone, the arrangement of the present invention can be used to monitor density fluctuations in the flow over a wide range. Further, the readings from the nuclear density gauge can be used to adjust the parameters in the operation of the hydrocyclone in order to maintain its operation at peak efficiency.

46 Claims, 6 Drawing Figures

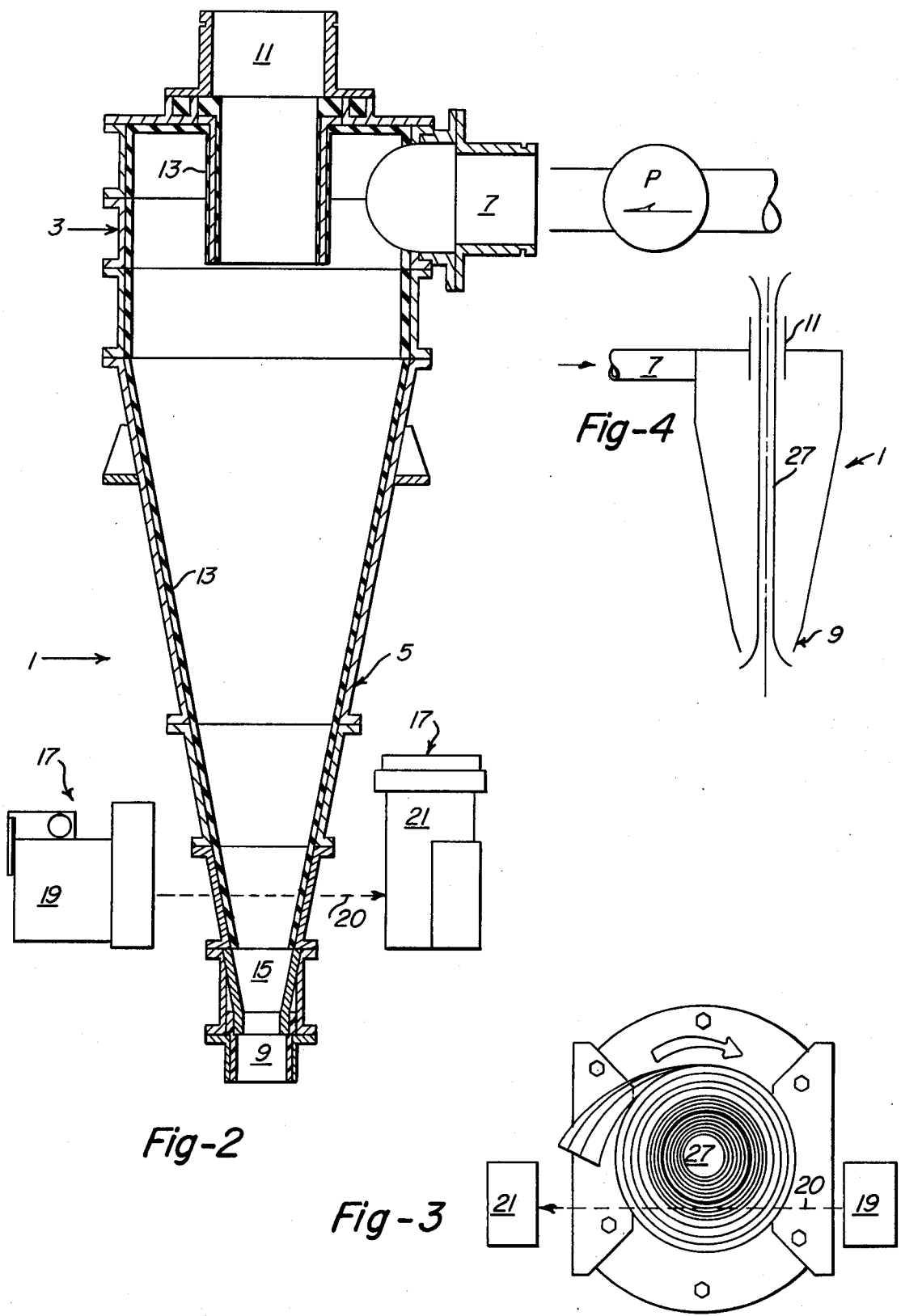

METHOD AND APPARATUS FOR MONITORING DENSITY FLUCTUATIONS IN MATERIAL FLOWING SPIRALLY WITHIN A HYDROCYCLONE

FIELD OF INVENTION

This invention relates to the field of nuclear density gauges and more particularly to the field of nuclear density gauges for use with hydrocyclones.

BACKGROUND OF THE INVENTION AND PRIOR ART

Nuclear density gauges are widely used in industry to monitor variations in flowing material. Essentially, these gauges consist of a source of radiation which is directed across the flow path of the material toward a detector. The source and detector are usually positioned exteriorly of the pipe, conduit, duct, hopper, or other device through which the material is flowing and as the radiation (e.g. gamma radiation) passes through the flow, a portion of it is absorbed by the material in the flow. The amount of radiation absorbed by the material in a unit volume of the flow is directly proportional to the mass in that unit volume. The higher the mass, the more radiation is absorbed and the less radiation arrives at the detector. Since the amount of absorbed radiation is directly proportional to the mass of the unit volume, the radiation measured at the detector is, therefore, inversely proportional to the mass of the unit volume. The density of a material is its mass per unit volume and since the intensity of the radiation arriving at the detector is inversely proportional to it, fluctuations in the density of the flowing material can be easily and quickly determined by monitoring the fluctuations in the intensity of the radiation arriving at the detector. Depending upon the type of radiation (e.g. alpha, beta, gamma) and the material in the flow, the incoming radiation may be absorbed, scattered, or absorbed and scattered by the material; however, in all of these circumstances, the intensity fluctuations in the transmitted radiation arriving at the detector are still inversely proportional to the mass per unit volume and can be used to accurately monitor density fluctuations in the flowing material.

Nuclear density gauges are safe, accurate, and reliable. In many instances, they are preferred over other measuring techniques because they do not interfere with the flow and can give a continuous reading of the condition of the flow. Further, unlike measuring techniques such as sampling, the flow being monitored by the nuclear density gauge need not be removed from the pipe, hopper, or other device. This is especially important in situations where the material is difficult to handle, messy, or cannot be removed from the pipe, hopper, or other device without affecting the very property or properties being measured.

The source of radiation in a nuclear density gauge is generally a radioactive material emitting high energy photons. Gamma radiation is widely used in nuclear density gauges because it is relatively unaffected by the chemical composition of the material and the amount of gamma radiation absorbed by the material is directly proportional to its mass. Cesium 137, strontium 90, and like elements whose radioactive half-life is sufficiently long for practical use are typical sources of gamma radiation that are used in nuclear density gauges. Other commercially available density gauges include those using lower electromagnetic radiation than that emitted by radioactive materials and those using sound waves in place of any radiation.

Nuclear density gauges are commonly used as on-off switches and warning devices that react to the absence or presence of a single, predetermined condition in material flowing through a duct, pipe, conduit, hopper, or the like. They are also commonly used to monitor fluctuations in the overall density of a flow and, in certain circumstances, they can further be used to accurately monitor fluctuations in the amount of a single component in the flow. For a nuclear density gauge to be able to monitor fluctuations in the amount of a single component in a flow, the flow must have only two components and one of the components must have a fixed specific gravity. In a two-component flow where one component has a fixed specific gravity (e.g. water), variations in the amount of the second component (e.g. particulate solids) will cause a predictable change in the radiation received by the detector. If a third component is present in the flow, it will adversely affect the accuracy of any readings because it represents a second, uncontrolled variable. The problems presented by a third component are particularly acute if its specific gravity is drastically different from that of the other components. For example, in a slurry of water (specific gravity 1.00) and particulate solids (specific gravity 2.7), the presence of air (specific gravity 0.001) in any significant amount as bubbles, an air column, an air core, or the like will make it impossible to use a nuclear density gauge to monitor fluctuations in the density of the particulate solids in the flow. In such three-component flows, there is no way to accurately determine the relative portion of the radiation arriving at the detector that is due to the presence of air as opposed to the presence of particulate solids.

U.S. Patents and Defensive Publications filed in the U.S. Patent Office that illustrate the use of nuclear gauges as on-off type switches or warning type devices reacting to a single variable or condition in the flow are: U.S. Pat. No. 3,796,692 to Foltz et al. issued on Mar. 12, 1974, U.S. Pat. No. 3,545,735 to Wolf et al. issued on Dec. 8, 1970, and Defensive Publication T913,010 by Arnold et al. corresponding to U.S. Patent application Ser. No. 341,475 filed on Mar. 15, 1973. The patent to Foltz involves a polymerization process in which a preferred level 30 of molten polymer in reactor 18 is first determined. Radiation from source 32 is then passed through the reactor 18 at the preferred level 30 along a horizontal path toward the radiation sensor 34. The absence or presence of molten polymer at level 30 is then sensed and Foltz's controls operated accordingly to maintain the molten polymer at the level 30. In a substantially corresponding manner, Wolf uses vertically spaced radioactive indicators at 14 and 15 to activate the closure valve 3 in response to the sensing of a maximum and minimum level of dust in the container 2 by the indicators. In the Defensive Publication of Arnold, nuclear density gauges are set up along a pipeline to react to the presence of sand in the normal well fluid. As explained by Arnold, the nuclear density gauges "can be set to energize an alarm, immediately or after a preset time delay, when the detected specific gravity of the well fluid varies beyond a preset minimum and/or maximum."

Numerous U.S. patents illustrate the use of nuclear density gauges to monitor density fluctuations in material flowing through a conduit, hopper, or the like. Among these are: U.S. Pat. No. 3,582,647 to Figuet et al. issued on June 1, 1971, U.S. Pat. No. 3,529,153 to Zimmerman et al. issued on Sept. 15, 1970, U.S. Pat. No. 3,281,594 to Garrison issued on Oct. 25, 1966, U.S. Pat. No. 3,128,786 to Badgett issued on Apr. 14, 1974, U.S. Pat. No. 3,106,933 to Kloppel issued on Oct. 15, 1963, U.S. Pat. No. 3,577,158 to Hahn issued on May 4, 1971 and U.S. Pat. No. 3,208,592 to Smith issued on Sept. 28, 1965. Figuet uses his nuclear density gauge to monitor density fluctuations in particulate solids flowing through a hopper 1. He also employs his nuclear density gauge as an on-off switch which responds to the absence or presence of material at a predetermined level in the hopper 1. Zimmerman's nuclear density gauge 1 is used to monitor density fluctuations in material flowing through his pipe 2. Garrison and Badgett each illustrate a nuclear density gauge in use monitoring a flow of sludge passing through a pipe. Kloppel's nuclear density gauge monitors density fluctuations in material at the bottom of a sedimentation tank 23. The material being monitored by Kloppel has a liquid phase and a solid phase. In the patent to Hahn, a nuclear density gauge is used to monitor density fluctuations in a flow passing through the conduit 12. Smith employs a plurality of nuclear density gauges 22, 23, and 25 to monitor density fluctuations in pipe flows leading into and out of his tank 10. Each of Smith's control valves 18, 19, and 20 is activated in response to the various readings of the gauges in order to maintain the operation of his device within certain, preset limits.

Nuclear density gauges have also been used with cyclone separators in which the carrier fluid is either a gas or a liquid. Cyclone separators in which the carrier liquid is water are commonly called hydrocyclones and examples of hydrocyclones are: U.S. Pat. No. 3,243,043 to Thompson et al. issued on Mar. 29, 1966, U.S. Pat. No. 3,912,579 to Braun issued on Oct. 14, 1975, U.S. Pat. No. 3,928,186 issued to Zemanek on Dec. 23, 1975, and U.S. Pat. No. 3,334,516 issued to Cedrone on Aug. 8, 1967. In these patents, a flow of particulate solids in water enters the hydrocyclone tangentially through a inlet near the top and begins moving downwardly along a spiral path toward a lower, first outlet. As the flow spirals downwardly, the heavier, particulate solids are thrown outwardly by centrifugal force. The separated particulate solids continue downwardly and exit the hydrocyclone through the lower, first outlet. As the heavier, particulate solids move outwardly, they displace the water and any lighter, particulate solids inwardly toward the middle of the hydrocyclone. The displaced water and lighter, particulate solids exit from the hydrocyclone through a second outlet that is positioned near the top of the hydrocyclone.

To date, no known hydrocyclone operation involving a hydrocyclone design with an inlet and at least first and second outlets such as the ones of Braun, Zemanek, Thompson, and Cedrone has been able to use a nuclear density gauge to monitor density fluctuations over a wide range in the flow within the hydrocyclone. The only known use of a nuclear density gauge in such hydrocyclones is as an on-off switch or warning device to detect the absence or presence of an air core or air column at a particular location within the hydrocyclone. In this known use, the beam of radiation is directed across the hydrocyclone to intersect the hydrocyclone's axis of symmetry between the inlet and the lower, first outlet. The existence or absence of the air core or air column along the axis of symmetry as detected by the nuclear density gauge indicates whether or not the hydrocyclone is operating properly. The existence of this air column in hydrocyclones of the design discussed above is believed to be a result of the spiralling or cyclonic action of the flow within the hydrocyclone and air entrained in the flow or aspirated into the hydrocyclone through the lower, first outlet.

The only known hydrocyclone operation in which a nuclear density gauge is directed across the hydrocyclone and is used to determine the mass of particulate solids being conveyed in the water is U.S. Pat. No. 4,010,369 to Daellenbach et al issued on Mar. 1, 1977. The hydrocyclone of Daellenbach is different both in structure and in operation from the much more common design of hydrocyclones as illustrated by the above-identified patents to Braun, Thompson, Zemanek and Cedrone and as illustrated by the hydrocyclone of the present invention. Daellenbach has a series of hydrocyclones which are inverted and which do not have the customary discharge orifice at the apex end. As shown in his FIG. 4, gamma radiation is directed diametrically across the apex end of the inverted hydrocyclones. The hydrocyclones are connected in cascade as shown in his FIG. 3 so that the overflow from the bottom of one hydrocyclone is supplied as feed to the next hydrocyclone. The purpose of Daellenbach's system is to make an analysis of particle size and mass distribution of the particulate solids in the water. The particle size of each succeeding hydrocyclone is smaller and the variously sized particles are separated out in the apex ends of the cyclones. By measuring across each apex, Daellenbach can then determine the mass of the separated particles in that apex. Daellenbach's hydrocyclones have a single inlet and a single outlet unlike the more common design in which the downwardly tapering cone of the hydrocyclone has an inlet near the top, a first lower outlet at the apex of the cone, and a higher, second outlet near the top of the cone. The hydrocyclones of Daellenbach do not have the problem with air cores or air columns that are present in the more common design and use of hydrocyclones as illustrated by the patents to Braun, Thompson, Zemanek and Cedrone and as employed in the environment of the present invention.

The patents discussed above relate primarily to the use of nuclear density gauges to measure conditions in a flow; however, nuclear density gauges have wide application and can be used, for example, to check the concentricity of tubes as illustrated by U.S. Pat. No. 3,109,095 to Van Horne issued on Oct. 29, 1963.

SUMMARY OF THE INVENTION

This invention involves a method and apparatus for monitoring density fluctuations in a spiralling flow of material and carrier liquid within a cyclone separator. In the preferred embodiments of the invention, a nuclear density gauge is used to monitor density fluctuations in the flow of particulate solids in water within a hydrocyclone. The hydrocyclone has an inlet near the top, a lower, first outlet, and an upper, second outlet located near the inlet. In response to a pressure differential set up between the inlet and the outlets, a flow of particulate solids in water enters the hydrocyclone tangentially through the inlet and begins moving downwardly along a spiral path toward the lower, first outlet. As the flow spirals downwardly, the heavier, particulate solids are thrown outwardly by centrifugal force.

The separated solids continue downwardly and exit the hydrocyclone through the lower or first outlet. As the heavier, particulate solids move outwardly, they displace the water and any lighter, particulate solids inwardly toward the middle of the cyclone. The displaced water and lighter, particulate solids exit from the hydrocyclone through the upper, second outlet.

The spiralling or cyclonic action of the flow creates an air column or air core extending along the axis of symmetry of the spiralling flow. The air in the air column is a result of air aspirated into the hydrocyclone through the lower, first outlet and air entrained in the incoming flow. Prior arrangements using nuclear density gauges directed the radiation diametrically across the center of the hydrocyclone and, because of the existence of the air core, the nuclear density gauge could only be used as an on-off type switch or warning device reacting to the normal presence or abnormal absence of the air column.

With the present invention, the nuclear density gauge can be used to monitor density fluctuations in the spiralling flow itself. This is accomplished by directing the beam of radiation of the nuclear density gauge asymmetrically across the hydrocyclone and spaced away from the air column. The radiation is preferably gamma radiation and the path of radiation can be directed perpendicularly to the axis of symmetry of the spiralling flow or at an inclined angle thereto. Preferably, the carrier liquid used has a constant specific gravity so that the fluctuations in the intensity of the radiation passing through the flow are inversely proportional to the amount of particulate solids in the flow. In each of the embodiments of the invention, the readings from the nuclear density gauge can then be used to adjust the parameters of the overall operation of the hydrocyclone to maximize its efficiency.

OBJECTS OF THE INVENTION

It is the primary object of this invention to provide a new and novel method and apparatus for monitoring density fluctuations in a spiralling flow of particulate solids in water within a hydrocyclone.

Another object of this invention is to provide a new and novel method and apparatus for using a nuclear density gauge to monitor density fluctuations in a spiralling flow of material and carrier liquid within a cyclone separator.

It is also an object to provide a new and novel method and apparatus for monitoring density fluctuations in material within a cyclone separator, which material is being conveyed in a carrier liquid with a substantially constant specific gravity.

Additional objects as well as features and advantages of this invention will become evident from the descriptions set forth hereinafter when considered in conjunction with the accompanying drawings.

BRIEF DESCRIPTION OF THE DRAWINGS

FIG. 2 is a cross-sectional view along line 2—2 of FIG. 1 showing the internal structure of the hydrocyclone.

FIG. 3 is a view along line 3—3 of FIG. 1 illustrating the preferred placement of the path of radiation relative to the centrally located air column.

FIG. 4 is a schematic view of the air column that is produced within the hydrocyclone as a result of air being aspirated into it through the lower outlet.

DETAILED DESCRIPTION OF THE PREFERRED EMBODIMENTS

Figure 1:
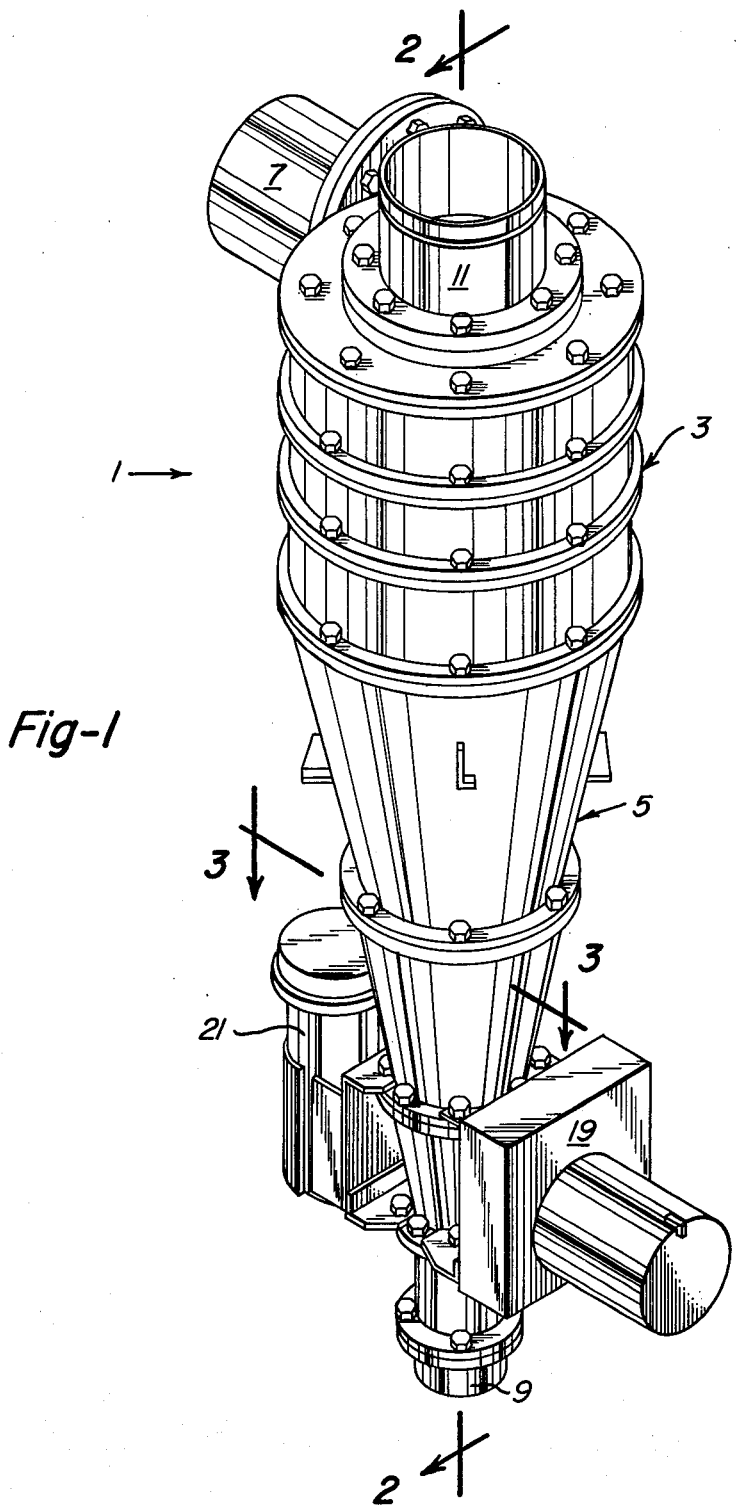
FIG. 1 is a perspective view of the invention showing the preferred positioning of the nuclear density gauge relative to the hydrocyclone.

As best seen in FIGS. 1 and 2, the hydrocyclone 1 of the present invention has an upper, cylindrical portion 3 and a downwardly tapering, conical portion 5. Inlet 7 to the hydrocyclone is positioned tangentially relative to the upper, cylindrical portion 3 and the hydrocyclone 1 has a lower, first outlet 9 and an upper, second outlet 11. Liners 13 are placed within the hydrocyclone 1 to protect its inner surfaces and apex valve 15 is positioned adjacent the lower outlet 9 as best seen in FIG. 2.

The nuclear density gauge 17 of the present invention is preferably placed adjacent the lower part of the conical portion 5 of the hydrocyclone 1 above the apex valve 15. The nuclear density gauge 17 includes a radiation directing means 19 and a radiation detector 21 positioned on opposing sides of the hydrocyclone 1. A source of radiation, preferably gamma radiation, is positioned within the directing means 19 which is surrounded for safety by lead walls. Commonly used sources of gamma radiation are Cesium 137, Cobalt 60 and Radium 226. The directing means 19 directs a beam of radiation along the path 20 across the hydrocyclone 1 toward the detector 21 which can be an ionization chamber, Geiger-Mueller tube, scintillation counter, or other conventional type of detector.

Figure 5:
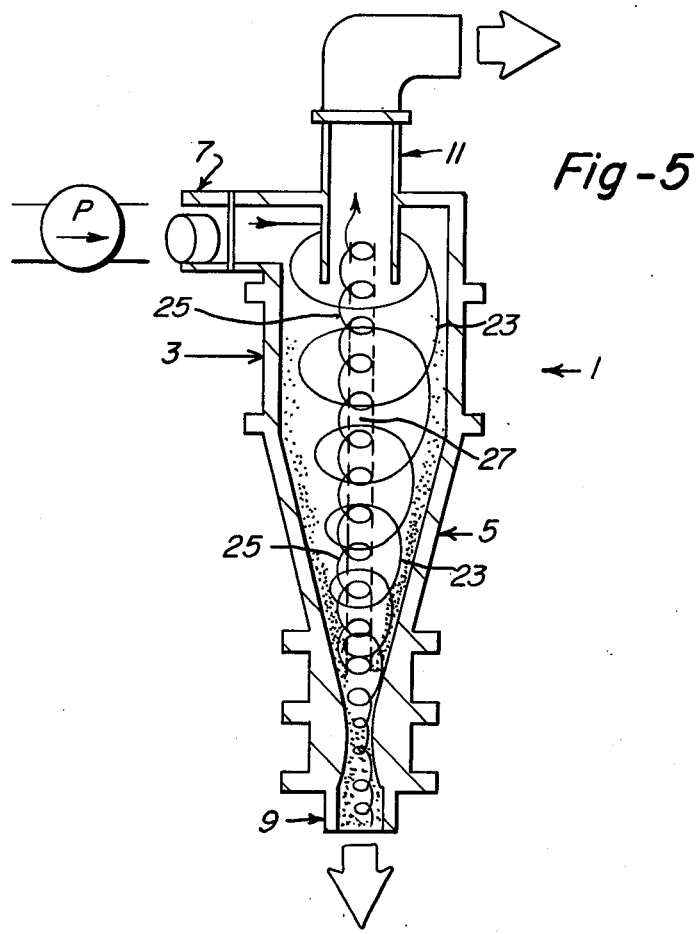
FIG. 5 is a schematic drawing of the spiralling flows and air column that are created within the hydrocyclone.

In operation, a flow of material and carrier fluid such as particulate solids and water enters the hydrocyclone 1 tangentially through inlet 7 in response to a pressure differential created by pump P between the inlet 7 and the outlets 9 and 11 as best seen in FIGS. 2 and 5. The flow moves downwardly toward the lower outlet 9 along a first spiral path 23 and the heavier, particulate solids are thrown outwardly by centrifugal force. The separated particulate solids continue downwardly and exit the hydrocyclone 1 through the lower outlet 9. As the heavier, particulate solids move outwardly, they displace the water and lighter particulate solids towards the middle of the hydrocyclone 1. Some of the water exits with the heavier, particulate solids through the lower outlet 9; however, most of the water and lighter, particulate solids exit the hydrocyclone 1 along a spiral path 25 through the upper outlet 11. The spiral path 25 extends interiorly of the spiral path 23 and the axes of symmetry of the hydrocyclone 1 and spiralling paths 23 and 25 are substantially colinear.

As a result of the spirally or cyclonic action of the flow, an air column or air core 27 is created within the hydrocyclone 1. The air column 27 extends substantially along the axis of symmetry of the first spiral path 23 and is believed to be a result of air aspirated into the hydrocyclone 1 through the lower outlet 9 (see FIG. 4) and/or air entrained in the incoming flow. FIG. 4 is a schematic view showing an air column 27 that is primarily created by the cyclonic action of the flow aspirating air into the hydrocyclone 1 through the lower outlet 9. The air column 27 can remain relatively stationary or can move upwardly through the outlet 11 along with the water and lighter, particulate solids.

The bottom of the air column 27 moves up or down depending upon whether the underflow through outlet 9 is sprayed or roped. As the underflow through outlet 9 becomes overloaded or roped, the bottom of the air column 27 moves upwardly. In past devices, the path of radiation from the nuclear density gauge 15 has been directed diametrically across the hydrocyclone 1 at a location where the bottom of the air column 27 should be for maximum efficiency of the operation of a hydrocyclone 1. Part arrangements use the nuclear density gauge in the environment of a cyclone separator such as hydrocyclone 1 to merely sense the presence or absence of the bottom of the air column 27 at the predetermined location. Such prior nuclear density gauges are used only as on-off type switches or warning devices to indicate a roped or overloaded condition within the hydrocyclone. Because the air in the air column 27 represents an uncontrolled, second variable, previous arrangements in which the path of radiation was directed across the center of the hydrocyclone were unable to use the nuclear density gauge to monitor density fluctuations in the spiralling flow within the hydrocyclone 1.

With the invention, the directing means 19 of the nuclear density gauge 17 directs a beam of radiation asymmetrically across the hydrocyclone 1 away from the air column 27 as illustrated in FIG. 3. In this manner, the density fluctuations in the spiralling flow 23 can be monitored. The path 20 of the radiation is preferably well spaced from the air core 27 and directed through the spiralling flow 23, however, it can be positioned as desired as long as it is still spaced from the air column 27. For example, the path 20 could be directed to intersect both spiralling flows 23 and 25 if desired. In the preferred operation, the carrier liquid has a substantially constant specific gravity so that the fluctuations in the intensity of the radiation received at the detector 21 will be inversely proportional to the amount of particulate solids in the flow.

Figure 6:
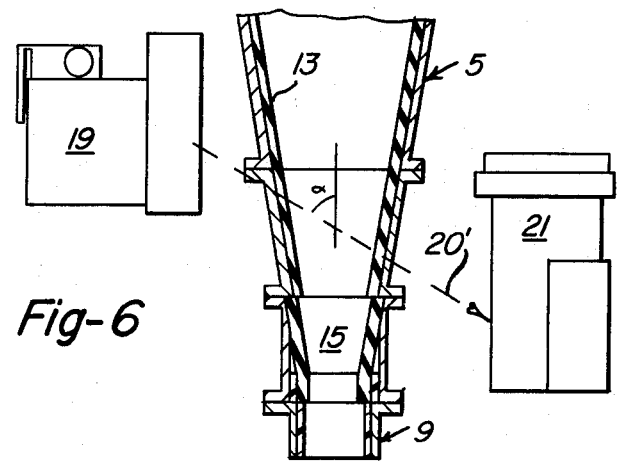
FIG. 6 illustrates a modification of the invention in which the radiation is directed along a path spaced from the air column and inclined at approximately 60 degrees to the axis of symmetry of the hydrocyclone and the axis of symmetry of the spiralling flows created within the hydrocyclone.

FIG. 6 illustrates a modification in which the beam of radiation is directed along a path 20' which is inclined at an angle alpha ($\alpha$) to the axis of symmetry of the hydrocyclone 1 and the axes of symmetry of the spiralling flows 23 and 25. In this manner, the radiation passes through a larger portion of the flow then the path 20 of the embodiment of FIG. 2 where the path 20 is substantially perpendicular to the axis of symmetry of the hydrocyclone 1. Theoretically, the readings from the arrangement of FIG. 6 would be more accurate than those from the arrangement of FIG. 2 because the radiation passes through a larger portion of the flow; however, in practical use, the difference in accuracy of the two arrangements is virtually neglagable. The angle alpha ($\alpha$) of inclination of the path 20' in the embodiment of FIG. 6 can be varied as desired. Preferably, it is about 60 degrees.

In an actual installation, the particular solids present may differ in particle size and chemical composition. For example, a screen analysis of ground ore solids present in the metallurgical slurry will show the presence of solids of a substantial size range and the composition of the particles may vary. While differences in particle size and composition are factors capable of causing variation in energy absorption for a given installation, where the source material being processed to produce the slurry remains generally the same and the processing is standardized, such factors will not seriously interfere with detection of changes in absorption of radiation resulting from changes in the amount of solids per unit volume of carrier liquid. Also as previously mentioned, variations in chemical composition do not materially affect the ability of the particles to absorb radiation.

By way of example, the apparatus and method can be installed in an ore processing system of the type in which ore is crushed and subjected to continuous wet milling in closed circuit with a classifier. The processed slurry is continuously delivered to hydrocyclones for further classification or dewatering. Assuming that one or more of the hydrocyclones are equipped with a nuclear density indicator according to the present invention, if the density of the slurry in the lower portion of the hydrocyclone varies from a desired normal value due to a change in the amount of solids per unit volume of the carrier, this is indicated to the operator by the detector. The detector may be connected to operate an alarm, a visual indicator or a recorder, or it may be connected to means which modifies the processing system, the flow rate of the slurry to the hydrocyclone and/or the adjustment of the apex valve of the hydrocyclone. The means thus actuated would cause the processing system and the hydrocyclone to return to the desired normal operation.

While several embodiments of the present invention have been described in detail herein, various changes and modifications can be made without departing from the scope of the invention.

We claim:

1. A method for monitoring density fluctuations in a flow of material and carrier liquid moving along a substantially symmetrical spiral path within a cyclone separator, said cyclone separator having an inlet and at least first and second outlets whereby material being conveyed in said carrier liquid enters said cyclone separator through said inlet in response to a pressure differential set up between said inlet and said first and second outlets, moves along said spiral path within said cyclone separator toward said first outlet, and has a portion thereof separated from said carrier liquid, said separated portion of said material exiting said cyclone separator through said first outlet and said separated carrier liquid and remaining portion of said material exiting said cyclone separator through said second outlet, said spiralling flow of material and carrier liquid further creating an air column within said hydrocyclone extending substantially along a portion of the axis of symmetry of said spiral path, said method comprising the steps of:
   (a) providing a source of radiation,
   (b) directing a beam of said radiation along a path intersecting at least a portion of said spiral path and spaced from said air column, and,
   (c) monitoring fluctuations in the intensity of at least a portion of said beam at a location along said radiation path downstream of said intersected portion of said spiral path, said intensity fluctuations in the monitored portion of said beam being proportional to density fluctuations in the material and carrier liquid flowing along said intersected portion of said spiral path.

2. The method of claim 1 wherein said material is particulate solids.

3. The method of claim 2 wherein said carrier liquid has a substantially constant specific gravity whereby said intensity fluctuations of step (c) are inversely proportional to fluctuations in the amount of particulate solids in the intersected portion of said spiral path.

4. The method of claim 3 wherein said carrier liquid is water and said cyclone separator is a hydrocyclone.

5. The method of claim 1 wherein the radiation of step (a) is gamma radiation.

6. The method of claim 1 wherein step (a) includes the further limitation of providing said source of radiation at a location exteriorly of said cyclone separator.

7. The method of claim 1 wherein step (c) includes the further limitation of positioning said monitoring location exteriorly of said cyclone separator.

8. The method of claim 1 wherein step (a) includes the further limitation of providing said source of radiation at a location exteriorly of said cyclone separator and step (c) includes the further limitation of positioning said monitoring location exteriorly of said cyclone separator.

9. The method of claim 1 wherein said radiation path of said beam in step (b) is substantially perpendicular to the axis of symmetry of said spiral path.

10. The method of claim 1 wherein said radiation path of said beam in step (b) is inclined at an angle to the axis of symmetry of said spiral path.

11. The method of claim 10 wherein said inclined angle is approximately 60 degrees.

12. A method for monitoring density fluctuations in material being conveyed in a carrier liquid along a substantially symmetrical spiral path within a cyclone separator, said method comprising the steps of:
(a) providing a source of radiation,
(b) directing a beam of said radiation along a path intersecting at least a portion of said spiral path and spaced from the axis of symmetry of said spiral path, and,
(c) monitoring fluctuations in the intensity of at least a portion of said beam at a location along said radiation path downstream of said intersected portion of said spiral path, said intensity fluctuations in the monitored portion of said beam being proportional to density fluctuations in said material and carrier liquid flowing along said intersected portion of said spiral path.

13. The method of claim 12 wherein said material is particulate solids.

14. The method of claim 13 wherein said carrier liquid has a substantially constant specific gravity whereby said intensity fluctuation of step (c) are inversely proportional to fluctuations in the amount of particulate solids in the intersected portion of said spiral path.

15. The method of claim 14 wherein said carrier liquid is water and said cyclone separator is a hydrocyclone.

16. The method of claim 12 wherein the radiation of step (a) is gamma radiation.

17. The method of claim 12 wherein step (a) includes the further limitation of providing said source of radiation at a location exteriorly of said cyclone separator.

18. The method of claim 12 wherein step (c) includes the further limitation of positioning said monitoring location exteriorly of said cyclone separator.

19. The method of claim 12 wherein step (a) includes the further limitation of providing said source of radiation at a location exteriorly of said cyclone separator and step (c) includes the further limitation of positioning said monitoring location exteriorly of said cyclone separator.

20. The method of claim 12 wherein said radiation path of said beam in step (b) is substantially perpendicular to the axis of symmetry of said spiral path.

21. The method of claim 12 wherein said radiation path of said beam in step (b) is inclined at an angle to the axis of symmetry of said spiral path.

22. The method of claim 21 wherein said inclined angle is approximately 60 degrees.

23. In a cyclone separator for separating particulate solids from a carrier liquid in which said cyclone separator has an inlet and at least first and second outlets whereby particulate solids being conveyed in said carrier liquid enter said cyclone separator through said inlet in response to a pressure differential set up between said inlet and said first and second outlets, move along a substantially symmetrical spiral path within said cyclone separator toward said first outlet, and has a portion thereof separated from said carrier liquid, said separated portion of said particulate solids exiting said cyclone separator through said first outlet and said separated carrier liquid and remaining portion of said particulate solids exiting said cyclone separator through said second outlet, said spiralling flow of particulate solids and carrier liquid further creating an air column within said cyclone separator extending substantially along a portion of the axis of symmetry of said spiral path, the improvement including:
means for providing a source of radiation,
means for directing a beam of said radiation along a path intersecting at least a portion of said spiral path and spaced from said air column, and,
means for monitoring fluctuations in the intensity of at least a portion of said beam at a location along said radiation path downstream of said intersected portion of said spiral path, said intensity fluctuations in the monitored portion of said beam being proportional to density fluctuations in the particulate solids and carrier liquid flowing along said intersected portion of said spiral path.

24. The improvement of claim 23 wherein said carrier liquid has a substantially constant specific gravity so that said intensity fluctuations are inversely proportional to fluctuations in the amount of particulate solids in said intersected portion of said spiral path.

25. The improvement of claim 24 wherein said carrier liquid is water and said cyclone separator is a hydrocyclone.

26. The improvement of claim 23 wherein said radiation is gamma radiation.

27. The improvement of claim 23 further including means for positioning said source of radiation at a location exteriorly of said cyclone separator.

28. The improvement of plan 23 further including means for positioning said monitoring means exteriorly of said cyclone separator.

29. The improvement of claim 23 further including means for positioning said source of radiation at a location exteriorly of said cyclone separator and means for positioning said monitoring means at a location exteriorly of said cyclone separator.

30. The improvement of claim 23 wherein said directing means directs said beam substantially perpendicular to the axis of symmetry of said spiral path.

31. The improvement of claim 23 wherein said directing means directs said beam at an inclined angle to the axis of symmetry of said spiral path.

32. The improvement of claim 31 wherein said inclined angle is approximately 60 degrees.

33. In a substantially symmetrical cyclone separator in which material and carrier liquid move along a substantially spiral path within said cyclone separator, the improvement including:

means for providing a source of radiation, means for directing a beam of said radiation along a path spaced from the axis of symmetry of said cyclone separator and intersecting a portion of said spiral path, and, means for monitoring fluctuations in the intensity of at least a portion of said beam at a location along said radiation path downstream of said intersected portion of said spiral path, said intensity fluctuations in the monitored portion of said beam being proportional to density fluctuations in the material and carrier liquid moving along said intersected portion of said spiral path.

34. The improvement of claim 33 wherein said material is particulate solids.

35. The improvement of claim 34 wherein said carrier liquid has a substantially constant specific gravity so that said intensity fluctuations are inversely proportional to fluctuations in the amount of particulate solids in the intersected portion of said spiral path.

36. In the improvement of claim 35 wherein said carrier liquid is water and said cyclone separator is a hydrocyclone.

37. The improvement of claim 33 wherein said radiation is gamma radiation.

38. The improvement of claim 33 further including means for positioning said source of radiation at a location exteriorly of said cyclone separator.

39. The improvement of claim 33 further including means for positioning said monitoring means exteriorly of said cyclone separator.

40. The improvement of claim 33 further including means for positioning said source of radiation at a location exteriorly of said cyclone separator and means for positioning said monitoring means at a location exteriorly of said cyclone separator.

41. The improvement of claim 33 wherein said directing means directs said beam substantially perpendicular to the axis of symmetry of said cyclone separator.

42. The improvement of claim 33 wherein said directing means directs said beam at an inclined angle to the axis of symmetry of said cyclone separator.

43. The improvement of claim 42 wherein said inclined angle is approximately 60 degrees.

44. In combination with a hydrocyclone of the type having a separating chamber that is annular in section and which has a tangential inlet at one end of the same, an under flow outlet at a second end, and an overflow outlet at said one end, the underflow and overflow outlets being aligned with the central longitudinal axis of the chamber, means for generating a beam of nuclear radiation disposed adjacent one side of the chamber, and means for detecting such radiation and variations in the intensity of the same disposed upon the other side of the chamber, the beam of radiation being directed through the chamber and through material within the chamber being subjected to separating forces, the path of the beam being spaced laterally from the axis of the chamber.

45. Apparatus as in claim 44 in which the generating and detecting means are so located that the beam is directed through the lower portion of the hydrocyclone chamber near the second end of the same.

46. Apparatus as in claim 44 in which said generating and detecting means are so located that the path of the radiation is positioned to pass through the heavier separated material in the lower portion of the chamber.

* * * * *